(12) United States Patent
Bhagwan et al.

(10) Patent No.: US 8,494,872 B2
(45) Date of Patent: Jul. 23, 2013

(54) PERSONALIZED ELECTRONIC HEALTHCARE MANAGEMENT

(75) Inventors: Varun Bhagwan, San Jose, CA (US); Tyrone W. A. Grandison, San Jose, CA (US); Christan E. Grant, Gainesville, FL (US); Bryan J. Hickerson, Atlanta, GA (US); Kun Liu, San Jose, CA (US); Evimaria Terzi, Palo Alto, CA (US); Tarun Thakur, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 307 days.

(21) Appl. No.: 12/700,339

(22) Filed: Feb. 4, 2010

(65) Prior Publication Data

US 2011/0191114 A1 Aug. 4, 2011

(51) Int. Cl.
G06Q 50/00 (2012.01)

(52) U.S. Cl.
USPC .................................. 705/2; 705/3

(58) Field of Classification Search
USPC ........................................ 705/2–3
See application file for complete search history.

(56) References Cited

U.S. PATENT DOCUMENTS

| | | | |
|---|---|---|---|
| 5,313,614 A | 5/1994 | Goettelmann et al. | |
| 5,842,017 A | 11/1998 | Hookway et al. | |
| 5,983,213 A | 11/1999 | Nakano et al. | |
| 6,748,558 B1 | 6/2004 | Gonzales et al. | |
| 2001/0032215 A1 | 10/2001 | Kyle et al. | |
| 2001/0037218 A1* | 11/2001 | Kaker et al. | 705/2 |
| 2001/0044811 A1 | 11/2001 | Ballantyne et al. | |
| 2002/0019910 A1 | 2/2002 | Pitsianis et al. | |
| 2003/0023955 A1 | 1/2003 | Bates et al. | |
| 2005/0014842 A1 | 1/2005 | Baumann et al. | |
| 2005/0027953 A1 | 2/2005 | McIntosh et al. | |
| 2005/0246693 A1 | 11/2005 | Plum | |
| 2006/0130021 A1 | 6/2006 | Plum et al. | |
| 2006/0200754 A1 | 9/2006 | Kablesh et al. | |
| 2007/0094048 A1 | 4/2007 | Grichnik | |
| 2007/0198296 A1* | 8/2007 | Pellinat et al. | 705/2 |
| 2007/0203753 A1 | 8/2007 | Hasan et al. | |
| 2007/0271121 A1 | 11/2007 | Laudan et al. | |
| 2007/0288266 A1 | 12/2007 | Sysko et al. | |
| 2008/0235567 A1 | 9/2008 | Raj et al. | |
| 2009/0299761 A1* | 12/2009 | Thakur et al. | 705/2 |

OTHER PUBLICATIONS

D. Isern, et al., "Using Aggregation Operators to Personalize Agent-Based Medical Services", KES 2006, Part II, LNAI 4252, 2006, pp. 1256-1263, Springer, Germany.

(Continued)

Primary Examiner — Sind Phongsvirajati
(74) Attorney, Agent, or Firm — Cantor Colburn LLP

(57) ABSTRACT

A personalized electronic healthcare management system and computer-implemented method thereof. The system includes a user interface configured to receive user profile information associated with a user as input by the user, and a server interfacing with the user interface. The server retrieves healthcare information from at least one external source, and provides the retrieved healthcare information to the user at the user interface. The healthcare information may be personalized to the user's needs. The server further retrieves social service program information from at least one host site, provides the retrieved social service program information to the user, and applies to at least one social service program of the at least one host site using the user profile information, when desired by the user, and retrieves interactive information to be presented to the user at the user interface.

14 Claims, 8 Drawing Sheets

OTHER PUBLICATIONS

Hong-Wei Yang, et al., "A Personalized Products Selection Assistance Based on E-Commerce Machine Learning", Proc. of 3rd International Conference on Maching Learning and Cybernetics, 2004, pp. 2629-2633, IEEE.

K. Abbas, et al., "Adaptive Context for Medical Information Systems", ICDIM'07, 2007 pp. 1-6, IEEE.

Syed Sibte Raza Abidi, "A Case Base Reasoning Framework to Author Personalized Health Maintenance Information", IEEE Symposium on Computer-Based Medical Systems (CBMS 2002), 2002, pp. 1-6, IEEE.

S. Abidi et al., "An Intelligent Info-Structure for Composing and Pushing Personalised Healthcare Information Over the Internet", 14th IEEE Symposium on Computer Based Medical Systems, 2001, pp. 225-230.

Jamia, [online]; [retrieved on Feb. 4, 2010]; retrieved from the Internet http://jamia.bmj.com/content/5/4/347.full.html S. McRoy et al. "Interactive Computerized Health Care Education," Journal of the American Medical Informatics Association, Jul./Aug. 1998, pp. 347-356, vol. 5 No. 4, BMJ group.

V. Curro et al., "Man-Machine Interfaces to Medical Information Systems", IEEE Engineering in Medicine & Biology Society 10th Annual International Conference—1341 CH2566-8/88/0000—1341, pp. 1-2, 1988, IEEE.

Yuri Quintana, [online]; [retrieved on Feb. 4, 2010] retrieved from the Internet www.yuriquintana.com/papers/Quintana-Information-Filtering.pdf Y. Quintana, "Intelligent Medical Information Filtering," 1998, 17 pages.

Cooper et al. "Building a Control-Flow Graph from Scheduled Assembly Code," Dept of Computer Science Rice University; 2002.

Djoudi et al., "MAQAO: Modular Assembler Quality Analyzer and Optimizer for Itanium 2", Workshop on EPIC Architectures and Compiler Technology; EPIC(4): pp. 1-20 (Mar. 2005) (San Jose, CA).

Office Action—Final for U.S. Appl. No. 12/130,094, filed Mar. 26, 2007; First Named Inventor: Wolfgang Gellerich; Mailing Date: Jul. 26, 2011 for U.S. Appl. No. 12/130,094.Jan. 4, 2012.

Office Action—Final for U.S. Appl. No. 12/130,094, filed May 30, 2008; First Named Inventor: Wolfgang Gellerich; Mail Date: Jan. 6, 2012.

Office Action—Non-Final for U.S. Appl. No. 12/130,094, filed May 30, 2008; First Named Inventor: Wolfgang Gellerich; Mail Date: Jul. 26, 2011.

Office Action—Non-Final for U.S. Appl. No. 11/690,978, filed Mar. 26, 2007; First Named Inventor: Wolfgang Gellerich; mail date Jul. 27, 2011; pp. 1-21.

Ward et al., "Legacy Assembler Reengineering and Migration", IEEE Computer Society; 20th ICSM (2004), pp. 157-166.

Notice of Allowance for U.S. Appl. No. 12/130,094, filed May 3, 2008; First Named Inventor: Wolfgang Gellerich; Mailing Date: Apr. 2, 2012.

Notice of Allowance for U.S. Appl. No. 11/690,978, filed Mar. 26, 2007; First Named Inventor: Wolfgang Gellerich; Mailing Date: Apr. 16, 2012.

* cited by examiner

PERSONALIZED ELECTRONIC HEALTHCARE MANAGEMENT

BACKGROUND

The present invention relates to electronic healthcare management, and more specifically, a personalized electronic healthcare management system capable of retrieving healthcare related information personalized to patients needs, and performing automated acquisition of the social service programs to help patients manage their medical conditions.

Today, the delivery of routine and emergency healthcare related information may be very time consuming. There is an increased burden in managing healthcare for rapidly aging populations, such as chronic diseases. There are also several concerns with establishing and resolving insurance coverage and medical treatment costs, and searching for and locating the relevant medical expertise that is familiar with a patient's condition and associated insurance information. In addition, there are concerns regarding maintaining longitudinal records of medicines and patient's family medical history, and finding and using the applicable governmental social support programs that would provide financial and social benefits are slowly being recognized as pivotal hindrances to providing a high standard of healthcare.

Currently there are massive amounts of healthcare information in cyberspace, ranging from government and business maintained resources to Web 2.0 user-generated content, e.g., wikis, blogs, and online healthcare discussion groups. Unfortunately, this information is not being effectively leveraged for several reasons such as the sources are diverse in syntax, semantics and structural representation and the sources are fragmented across a large distributed network. In addition, information regarding social support programs, such as transportation programs, financial assistance programs, and in-house support services, are not available in intuitive locations that are easily accessible to the patients. Further, patients have to rely on labor-intensive, manual, paper-based processes to work with administrators of these social programs, which normally lower the probability of acquiring benefits successfully.

SUMMARY

According to an embodiment of the present invention, a personalized electronic healthcare management system is provided which enables users to discover healthcare information e.g., financial, physical and informative information, and social services such as transportation programs, financial assistance programs, and in-house support services. In addition, the system provides intelligent analysis and deliver of healthcare information based on personalized needs and automated acquisition of the social services required to help patients manage their medical conditions.

According to an embodiment of the present invention, a personalized electronic healthcare management system is provided. The system includes a user interface configured to receive user profile information associated with a user as input by the user, and a server interfacing with the user interface. The server retrieves healthcare information from at least one external source and provides the retrieved healthcare information to the user at the user interface, retrieves social service program information from at least one host site, provides the retrieved social service program information to the user, and applies to at least one social service program of at least one host site using the user profile information, when desired by the user, and retrieves interactive information to be presented to the user at the user interface.

According to another embodiment of the present invention, a computer-implemented method is provided. The computer-implemented method includes receiving user profile information associated with a user as input by the user via a user interface, retrieving healthcare information from at least one external source and providing the retrieved healthcare information to the user at the user interface, and retrieving social service program information from at least one host site. The method further includes providing the retrieved social service program information to the user, applying to at least one social service program of the at least one host site using the user profile information, when desired by the user, and retrieving interactive information to be presented to the user at the user interface.

According to another embodiment of the present invention, a computer program product of the above-mentioned method is also provided.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Figure 1:
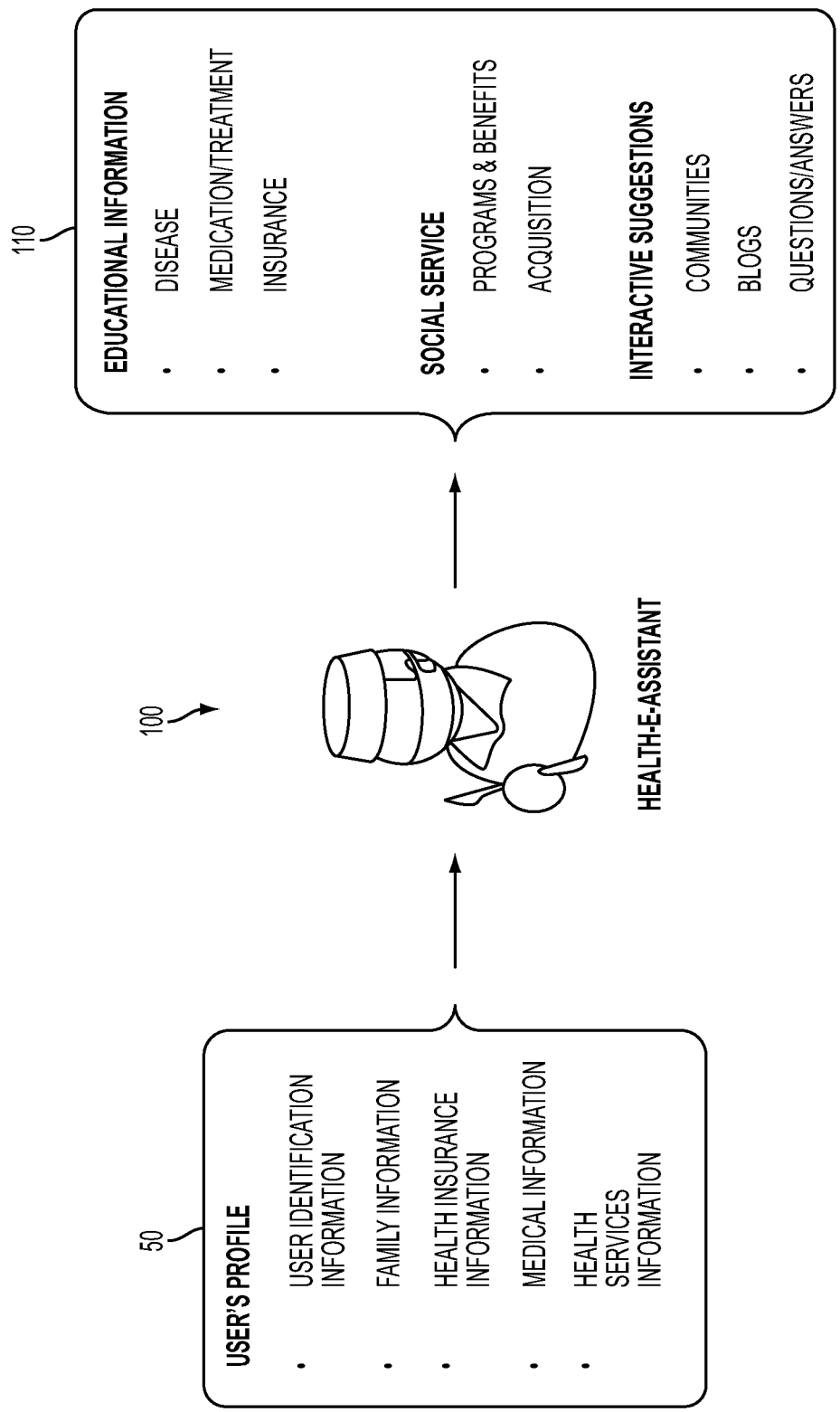
FIG. 1 is a block diagram illustrating a functional overview of the personalized electronic healthcare management system that can be implemented within embodiments of the present invention.

With reference now to FIG. 1, there is a block diagram illustrating a functional overview of a personalized healthcare management system 100 (i.e., a health-e-assistant "HeA") that can be implemented according to an embodiment of the present invention. As shown in FIG. 1, user profile information 50 is input into the personalized electronic healthcare management system 100. The user profile information 50 includes, for example, user identification information, family information, health insurance information, medical information and health services information input by the user and retrieved from third party sources. The system 100 retrieves and outputs various health-related information 110 from various external data sources, such as Wikipedia, WebMD, Mayo Clinic, Revolution Health, the FDA, and the Center for Disease Control and Prevention (CDC). However, the present invention is not limited to obtaining this information from any particular data source and any suitable source may be utilized. The healthcare information 110 may include healthcare educational information, social service information and interactive information for example. The healthcare educational information may include chronic disease information for hypertension, arthritis, chronic joint symptoms and heart disease, for example, medication and suggested treatment, and related insurance information which is personalized to correspond to the user profile information 50. The healthcare educational information may further include medical facility information regarding hospitals and clinics best suited for given medical conditions and comparative analysis of hospitals and clinics along with local nursing homes, home care and assist agencies in the user's demographic area and recent research studies. The social service information may include available social service programs and acquisition tools for users to acquire services provided by the social service programs. The interactive information may include online communities and blogs where users with similar medical conditions discuss various issues thereby providing real-time information, and interactive query usage to receive questions from the users and provide answers. Additional details regarding the personalized healthcare management system will now be discussed below with reference to FIG. 2.

Figure 2:
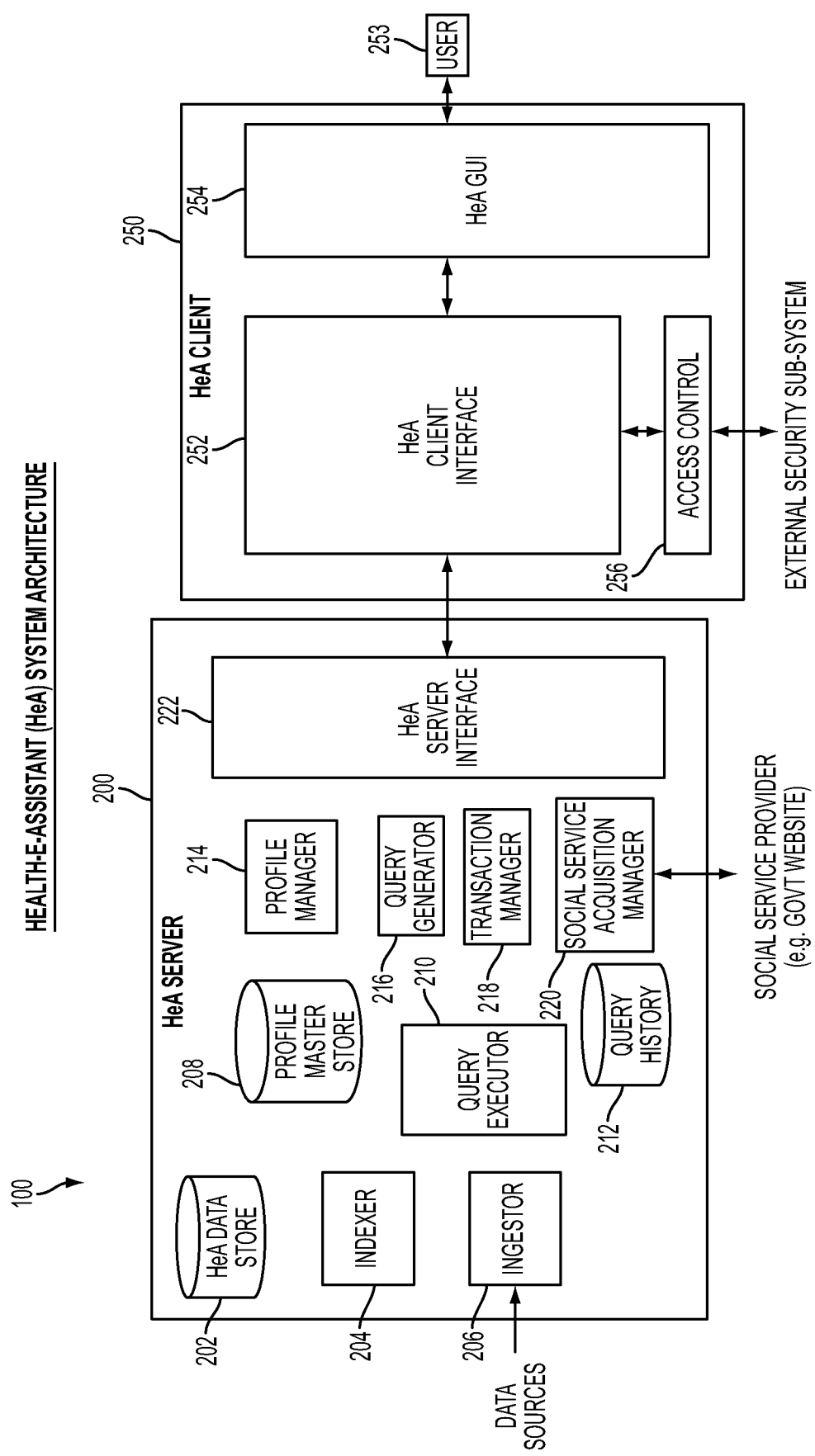
FIG. 2 is a block diagram illustrating a personalized electronic healthcare management system that can be implemented within embodiments of the present invention.

FIG. 2 is a block diagram illustrating a personalized healthcare management system 100 that can be implemented within embodiments of the present invention. As shown in FIG. 2, the system 100 includes a server 200 (i.e., HeA server) and a client 250 (i.e., HeA client) which interacts with the server 200. The server 200 includes a storage device (i.e., HeA data store) 202 for storing healthcare information, an indexer 204 for indexing healthcare information, an ingestor 206 for retrieving the healthcare information from various data sources, a profile master storage medium (i.e., the profile master store) 208 for storing profile information pertaining to each user 253, a query executor 210 for executing a query at the request of a user 253 of the system 100, a query history storage medium 212 for storing the query history information and providing a query history table to be viewed by the user 253, a profile manager 214 for managing user profile information within the system 100, a query generator 216 for generating a query at the request of a user 253, a transaction manager 218 which tracks/manages all transactions performed within the system 100, a social service acquisition manager 220 for acquiring social service information and a server interface 222 to interface with the client 250. According to an embodiment, the data store 202, the profile master store 208 and the query history storage medium 212 are secured storage locations. The query history storage medium 212 also provides the query history table to allow entries input by the user 253 to be viewed by the user 253. The client 250 includes a client interface 252, a graphical user interface (GUI) 254 and an access control module 256. The GUI 254 allows the user 253 to interact with the system 100 via the server interface 222.

According to an embodiment, the client interface 252 includes an access control facility 256 which may link to an external security sub-system service. The client interface 252 authenticates the user 253 by retrieving profile information associated with the user 253. According to an embodiment of the present invention, each user 253 is required to set up a profile in order to access the personalized healthcare management system 100. The system 100 facilitates user profile management, querying and assistance with external social service programs available at host sites.

According to an embodiment of the present invention, during an operation of the system 100, the GUI 254 receives user profile information associated with each user 253 as input by the user 253 and/or retrieved from third party sources. The server 200 continuously retrieves healthcare information from at least one external data source as mentioned above, via the ingestor 206. According to an embodiment, the healthcare information is focused for each user 253 based on the user profile information at the time that a query is issued, and the server 200 provides the retrieved healthcare information to the user 253 at the GUI 254. The server 200 also retrieves social service program information from at least one host site (i.e., a Social Service provider), provides the social service program information to the user and applies to at least one social service program of the at least one host site using the user profile information, when desired by the user 253. In addition, the server 200 retrieves interactive information to be presented to the user 253 at the GUI 254. According to an embodiment of the present invention, the interactive information may be both synchronous and asynchronous in nature. Additional detailed information regarding each element of the system 100 and interactions between each element will now be described below with reference to FIGS. 3 through 8.

First, operations for creating, updating and deleting a user profile will now be described below with reference to FIGS. 3 and 4.

Figure 3:
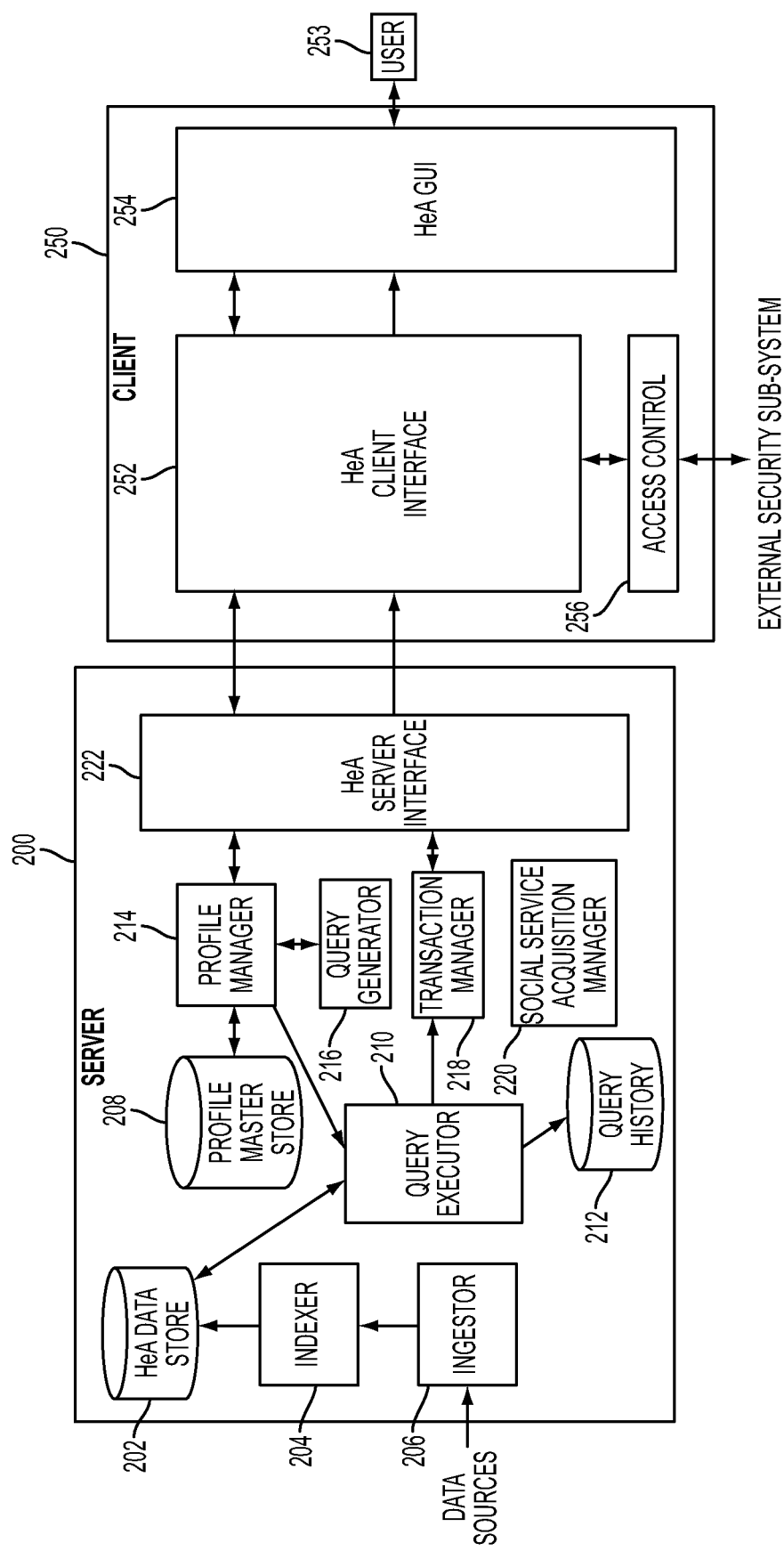
FIG. 3 is a flow diagram for creating and updating a user profile for the system shown in FIG. 2 that can be implemented within an embodiment of the present invention.

FIG. 3 is a flow diagram for creating and updating a user profile for the system shown in FIG. 2 that can be implemented within an embodiment of the present invention. As shown in FIG. 3, in order to create a user profile, a user 253 first creates an account by registering and creating a username and password, for example via the GUI 254. Alternate tokens may be used instead of or in conjunction with username and password. According to an embodiment of the present invention, a correctly authenticated user must have an associated profile ID prior to performing any queries using the system 100. Profile IDs are associated with usernames when a profile is created. The user 253 issues a request via the GUI. The profile request is compiled into an extensible markup language (XML) package, for example and sent from the client interface 252 asynchronously to the server interface 222 and the client 250 awaits a reply from the server 200. The server interface 222 first creates a transaction ID for this request and logs it with the Transaction Manager 218. The transaction manager 218 creates a template of expected results for the transactions which includes all the data to be displayed to the user 253. According to an embodiment of the present invention, the transaction ID is attached to all calls within the server 200. The server interface 222 then makes a "create" call to the profile manager 214. The profile manager 214 creates a new profile ID and removes the profile data and inserts it into the profile master store 208 and sends the newly generated profile ID to the query generator 216 where a personalized query request object is created. According to an embodiment of the present invention, the profile manager 214 logs the "create profile" operation performed, the time of the operation and the user 253 who issued the request, with the profile master store 208. The profile manager 214 then sends the query request object to the query executor 210 and the query executor 210 inserts the profile ID of the user 253, a query number, an actual query statement and an associated time stamp into the query history storage medium 212. The query executor 210 then inserts the results of its query into the transaction manager 218. The query executor 210 determines whether it is the last operation to update the transaction manager 218. That is, the query executor 210 determines whether other operations have been completed and if it determines that it is the last operation to be completed, it asserts a complete flag and notes a result returned timestamp with the query history table 212.

The server interface 222 retrieves transaction information from the transaction manager 218 to view the completed transactions, obtains the query results and profile ID, filters certain information such as some individual user information about the queries from the results and sends the results back to the client interface 252 of the client 250. Upon receiving the results of the create profile, the client interface 252 associates the newly created profile ID with the username, i.e. the authentication token(s), via the access control 256 and creates default widgets which access this information and updates the GUI 254. According to an embodiment of the present invention, the widgets independently access the information as desired to create an output to the GUI 254.

The process for updating a user profile is similar to that of creating the user profile as shown in FIG. 3 except the associated profile ID is retrieved after successful authentication of the user 253 via the client interface 252 in communication with the access control 256 and the user 253 is able to update his or her profile information via the client interface 252. According to the current embodiment, the profile manager 214 does not need to create a new profile ID and the client interface 252 does not associate the profile ID with the associated username when the results are returned to it. Instead, in order to update a user profile, after being authenticated, the user 253 inputs a request and required information via the GUI 254. The request and information input are sent to the server 200 via the client interface 252 and the server 200 processes the request and required information in the same manner as that of creating the user profile as previously mentioned above. A process for deleting a user profile will now be discussed below with reference to FIG. 4.

Figure 4:
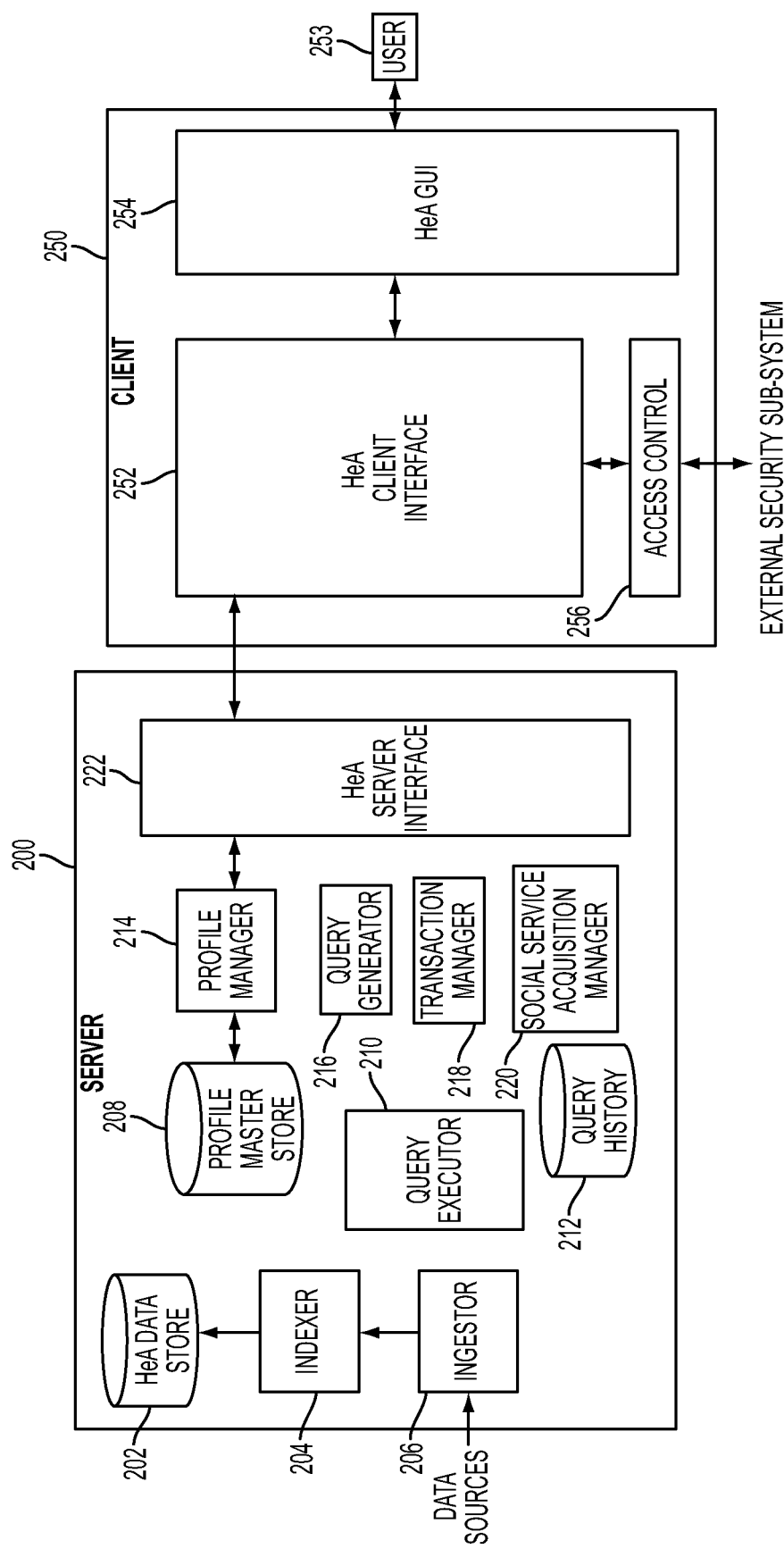
FIG. 4 is a flow diagram for deleting a user profile for the system shown in FIG. 2 that can be implemented within an embodiment of the present invention.

FIG. 4 is a flow diagram for deleting a user profile for the system 100 shown in FIG. 2 that can be implemented within an embodiment of the present invention. The process of deleting a user profile is similar to the processes for creating and updating a user profile. In order to delete a user profile, the user 253 makes a request to delete his or her user profile via the GUI 254. The request is sent to the client interface 252 which in turn forwards it to the server interface 222 of the server 200. The request is then sent to the profile manager 214 and the manager forwards the associated profile ID to the profile master store 208 to be removed. Once the profile ID of the user 253 is removed from the profile master store 208, a notification is sent to the client 250 via the server interface 222 and the client interface 252 disassociates the profile ID from the authenticated username. In addition, according to an embodiment of the present invention, all the associated metadata of the user 253 such as pending notifications from previous actions may be deleted from pending work in the system 100.

According to an embodiment of the present invention, upon creating a user profile, the user 253 is able to perform queries to retrieve general healthcare information and healthcare information personalized based on the user's profile. A process of performing queries using the system 100 according to embodiments of the present invention will now be described below with reference to FIGS. 5 and 6.

Figure 5:
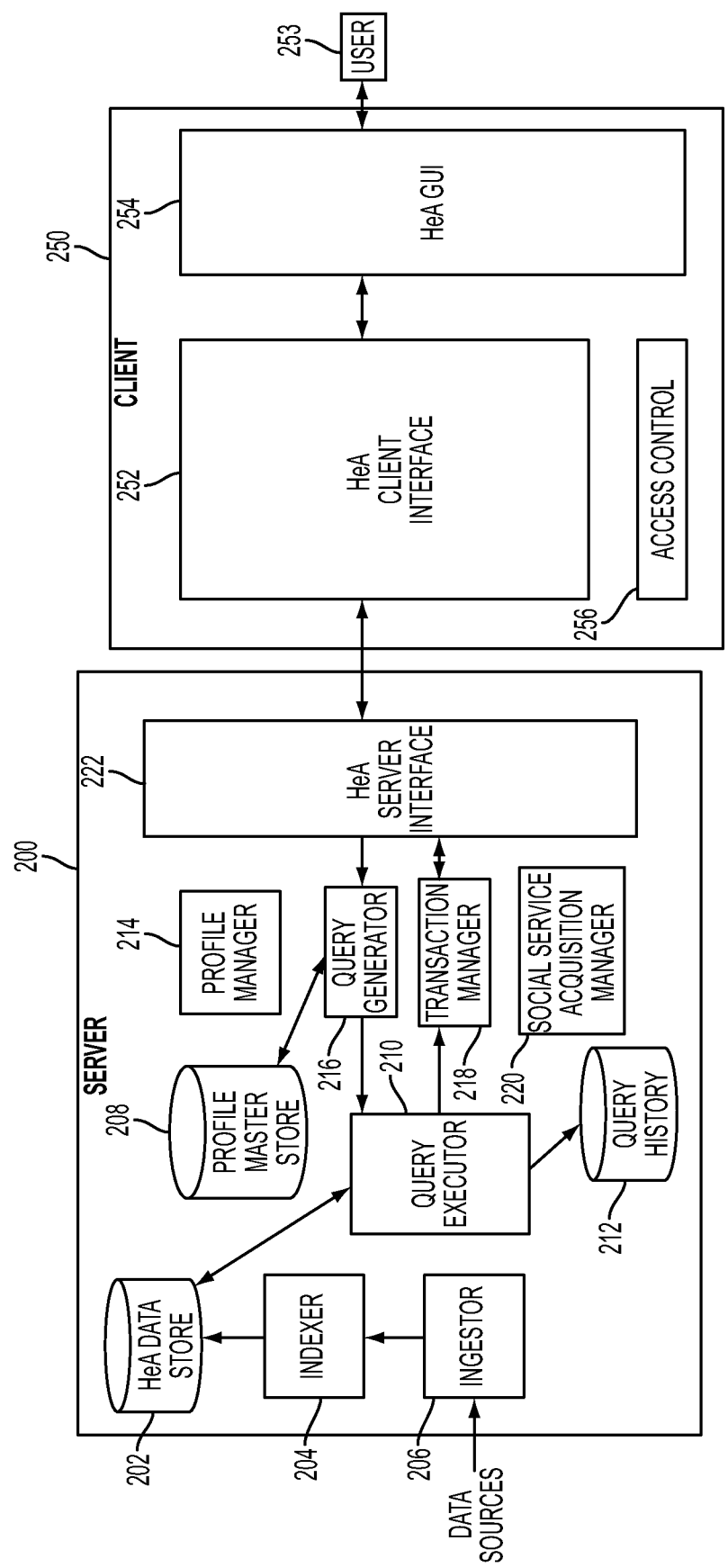
FIG. 5 is a flow diagram for executing personalized queries using the system shown in FIG. 2 that can be implemented within an embodiment of the present invention.

FIG. 5 is a flow diagram for executing personalized queries using the system shown in FIG. 2 that can be implemented within an embodiment of the present invention. As shown in FIG. 5, the user 253 may enter into their request into a search box, for example, at the client interface 252 and the user 253 may choose whether or not to personalize the query before submitting the search request. According to an embodiment of the present invention, personalization is only possible if there is an associated profile ID for the current session, i.e. if the user 253 has entered profile data. After submission, the request is sent from the client interface 252 to the server interface 222. In the server interface 222, a transaction ID is created and the request is recorded with the transaction manager 218. The server interface 222 then invokes the query generator 216. The query generator 216 then generates a query and sends the generated query to the query executor 210. If the query is to be personalized, the query generator 216 sends a request to the profile master store 208 for the profile data associated with the current profile ID. The query executor 210 logs the query with the query history storage medium 212 and issues the queries to the data store 202 and the query results are compiled and organized for further processing. When completed, the query executor 210 records its results in the transaction manager 218 and marks it as complete and records the completion of the query to the query history storage medium 212. The server interface 222 views the transaction from the transaction manager 218 and obtains the query results and profile ID, filters certain information such as some individual user information about the queries from the result and sends the results to the client interface 252 to be viewed by the user 253.

Figure 6:
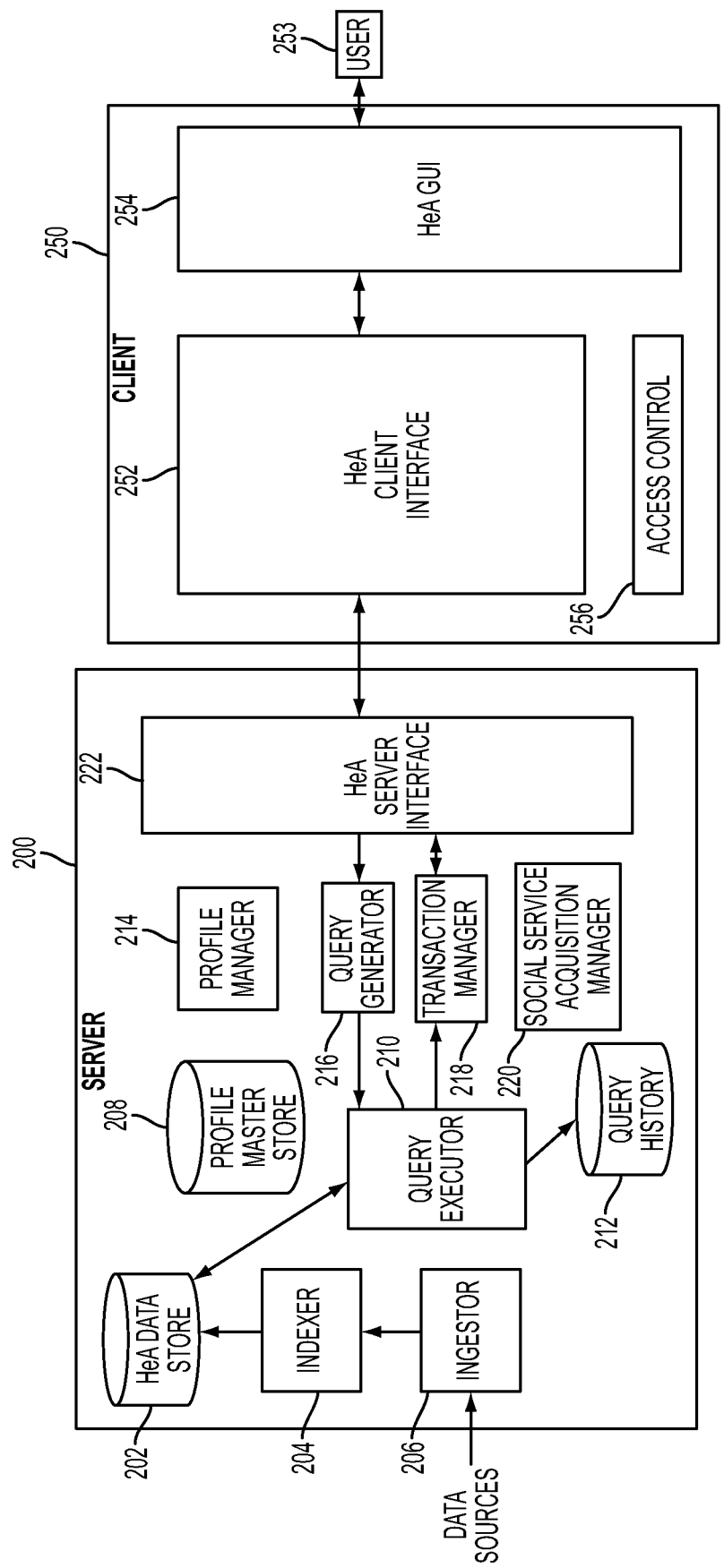
FIG. 6 is a flow diagram for executing non-personalized queries using the system shown in FIG. 2 that can be implemented within an embodiment of the present invention.
Figure 7:
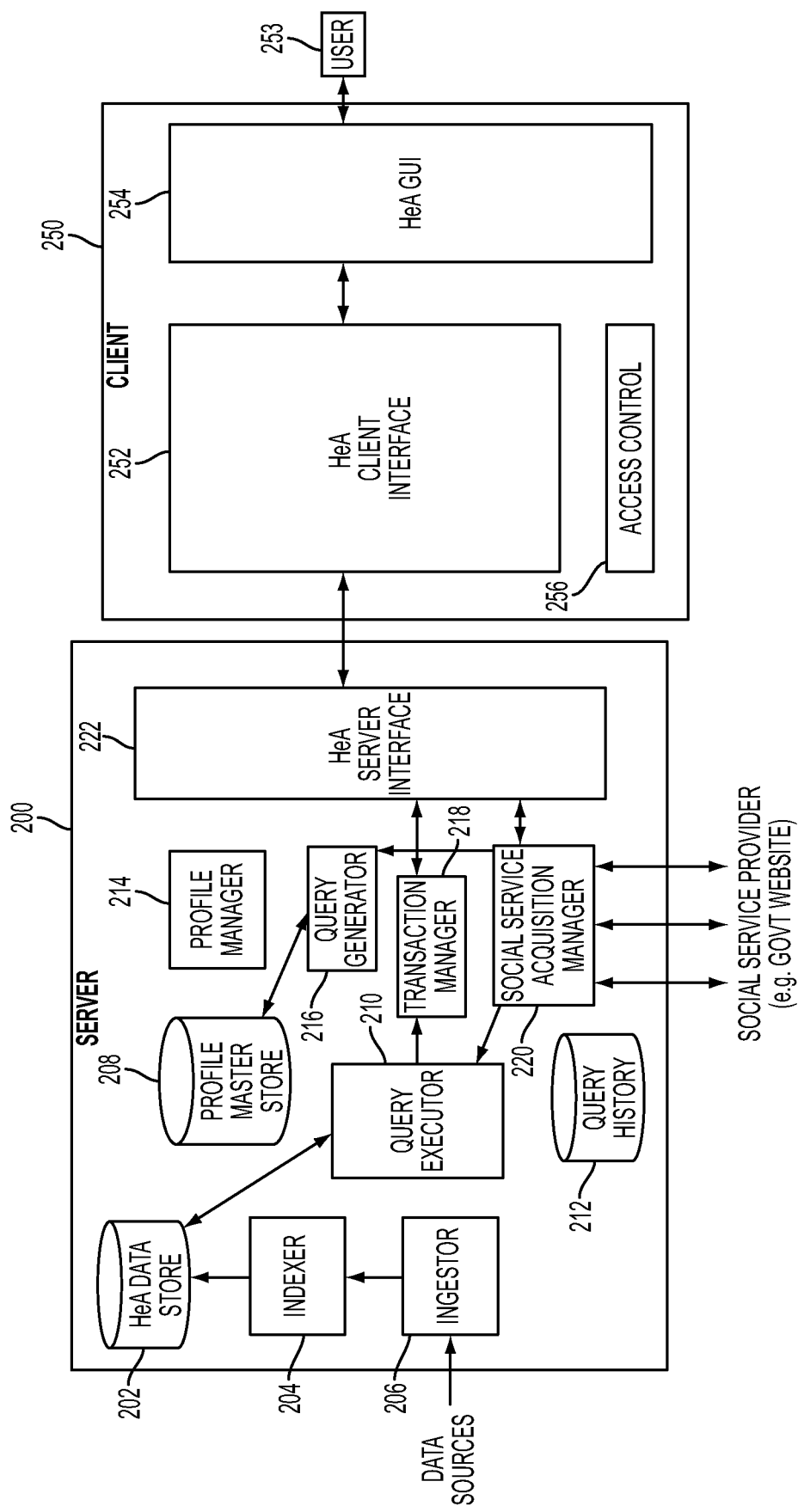
FIG. 7 is a flow diagram for requesting a social service program information using the system shown in FIG. 2 that can be implemented within an embodiment of the present invention.

FIG. 6 is a flow diagram for executing non-personalized queries using the system shown in FIG. 2 that can be implemented within an embodiment of the present invention. The process for performing a non-personalized query is similar to that of the personalized query except the user 253 elects not to personalize the query. As shown in FIG. 7, the query request is sent from the client interface 252 to the server interface 222. The server interface forwards the search request to the query generator 216 and the query generator 216 forwards the information associated with the search request to the query executor 210 which logs the query with the query history storage medium 212 and issues the queries to the data store 202 and the query results are compiled and organized for further processing. When completed, the query executor 210 records its results in the transaction manager 218 and marks it as complete and records the completion of the query to the query history storage medium 212. The server interface 222 then retrieves the transaction information from the transaction manager 218 and the query results and forwards the query results to the client interface 252 to be viewed by the user 253.

According to an embodiment of the present invention, some of the data returned in the course of creating a profile, updating a profile or issuing a query as described above with reference to FIGS. 3 through 6, may include social service information associated with social service programs that the user 253 may acquire. When a personalized query is performed, the social service information may include social service programs related to the user's profile information. These social service programs may be included in the healthcare information presented to the user 253 as a result of the query. When these services are presented to the user 253, the user 253 has an option of having the system 100 help the user 253 to acquire these services. Additional details concerning acquiring social service information according to an embodiment of the present invention will now be discussed below with reference to FIGS. 7 and 8.

FIG. 7 is a flow diagram for requesting a social service program using the system shown in FIG. 2 that can be implemented within an embodiment of the present invention. As shown in FIG. 7, upon request, the social service programs to be acquired along with the profile ID associated with a user 253 are sent to the server interface 222 via the client interface 252. The server interface 222 then creates a transaction and sends the request to the social service acquisition manager 220 in communication with a social service provider such as a government website, via the Internet, for example. The social service acquisition manager 220 sends a "generate forms" query to the query generator 216 and then passes the query to the query executor 210 for completion. The query executor 210 retrieves the forms from the data store 202. Once the forms are retrieved, the social security acquisition manager 220 automatically obtains the profile data associated with the user 253 by invoking the query generator 210 and retrieving the profile data from the profile master store 208 and completes the form using the user's profile data, the forms are then sent back to the client interface 252 for approval, feedback or additional user information needed.

Figure 8:
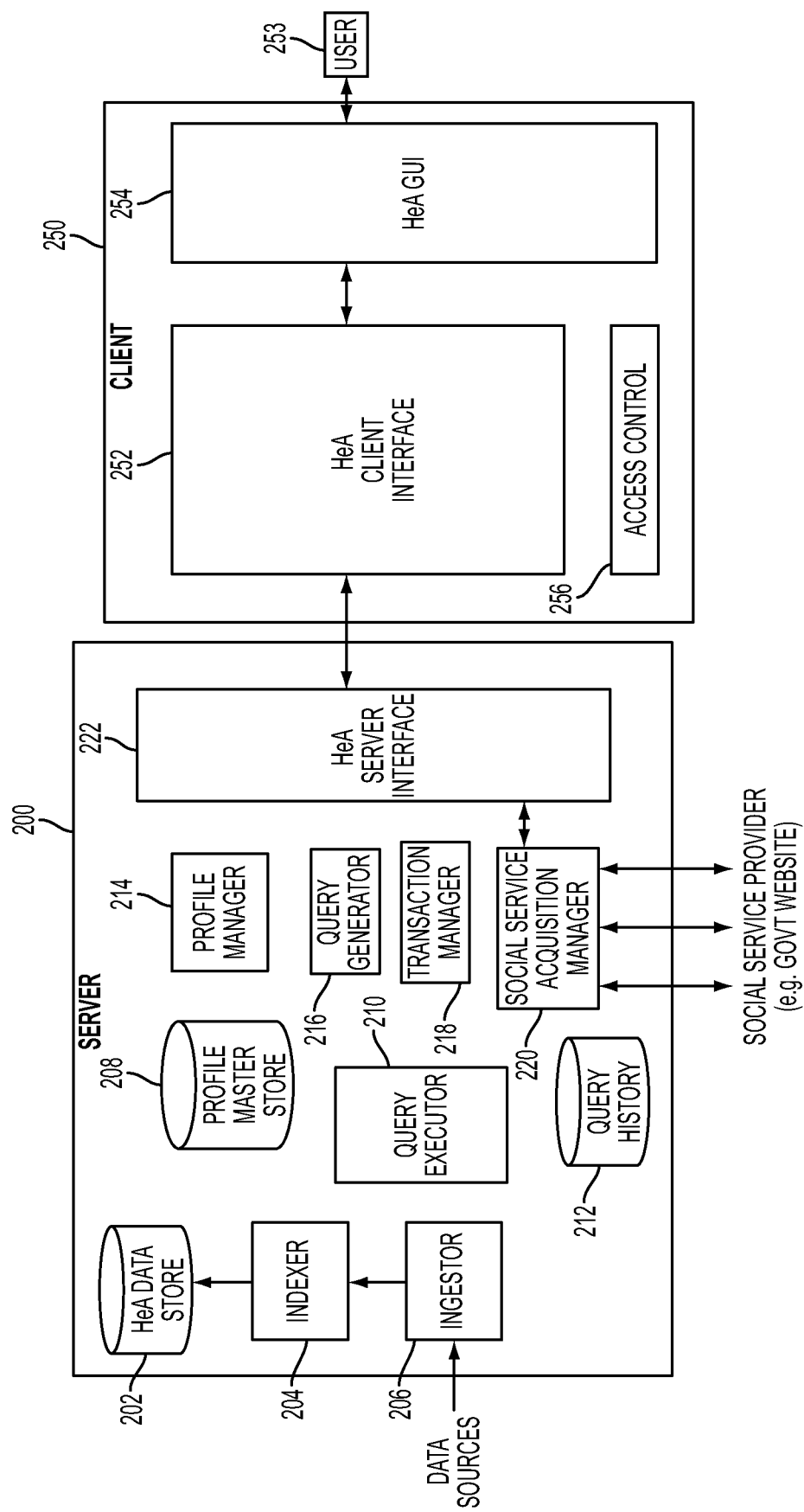
FIG. 8 is a flow diagram for submitting an application to a social service program using the system shown in FIG. 2 that can be implemented within an embodiment of the present invention

FIG. 8 is a flow diagram for submitting an application to a social service program using the system shown in FIG. 2 that can be implemented within an embodiment of the present invention. Once the forms have been completed as discussed above with reference to FIG. 8, the forms are sent back to the server interface 222 which logs the transaction and sends the forms to the social service acquisition manager 220 to oversee the acquisition/assignment process and the social service acquisition manager 220 sends the completed forms to the associated social service provider and sends progress updates back to the user 253 via the client interface 252 to keep the user 253 informed of the status of his/her application to the social service program.

The present invention provides a personalized healthcare management system which maintains user health information to keep the users informed and enables them to make better decisions about their health choices.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A personalized electronic healthcare management system, comprising:
    a user interface configured to receive user profile information associated with a user as input by the user, wherein the user profile information includes user identification information, family information, health insurance information, medical information; and
    a server interfacing with the user interface and configured to:
    retrieve healthcare information from at least one external source and provide the retrieved healthcare information to the user at the user interface;
    retrieve social service program information from at least one host site, provide the retrieved social service program information to the user, and apply to at least one social service program of the at least one host site using the user profile information, when desired by the user;
    retrieve interactive information to be presented to the user at the user interface, wherein the interactive information includes real-time information corresponding to online community information;
    retrieve at least one form for application to the at least one social service program when desired by the user;
    automatically obtain user profile information associated with the user to complete the retrieved form for application to the at least one social service program;
    submit the completed form to the at least one host site; and
    inform the user of a status of the application to the at least one social service program.

2. The electronic healthcare management system of claim 1, wherein the server is further configured to:
    provide interactive query usage by retrieving and organizing answers to a query performed by the user at the user interface.

3. The electronic healthcare management system of claim 2, wherein the server is configured to generate a personalized query or a non-personalized query as selected by the user via the user interface wherein when a personalized query is performed, the healthcare information retrieved is specific to the user based on the user profile information.

4. The electronic healthcare management system of claim 1, wherein the user profile information further comprises healthcare service information retrieved from third party sources.

5. The electronic healthcare management system of claim 1, wherein the healthcare information comprises healthcare educational information including chronic disease information and medical facility information.

6. A computer-implemented method, comprising:
receiving user profile information associated with a user as input by the user via a user interface of a client, wherein the user profile information includes user identification information, family information, health insurance information, medical information;
retrieving healthcare information from at least one external source and provide the retrieved healthcare information to the user at the user interface;
retrieve social service program information from a server interface, providing the retrieved social service program information to the user, and apply to at least one social service program of the server interface using the user profile information, when desired by the user;
retrieving interactive information to be presented to the user at the user interface, wherein the interactive information includes real-time information corresponding to online community information;
presenting the interactive information to the user via the user interface of the client;
retrieving at least one form for application to the at least one social service program when desired by the user;
automatically obtain user profile information associated with the user to complete the retrieved form for application to the at least one social service program;
submitting the completed form to the at least one host site; and
informing the user of a status of the application to the at least one social service program.

7. The computer-implemented method of claim 6, further comprising: providing interactive query usage by retrieving and organizing answers to a query performed by the user at the user interface.

8. The computer implemented method of claim 7, wherein providing interactive query usage comprises:
generating a personalized query or a non-personalized query as selected by the user via the user interface; and
retrieving healthcare information specific to the user based on the user profile information when a personalized query is performed.

9. The computer-implemented method of claim 6, wherein the user profile information further comprises healthcare service information retrieved from third party sources.

10. The computer-implemented method of claim 6, wherein the healthcare information comprises healthcare educational information including chronic disease information and medical facility information.

11. A non-transitory computer useable medium including a computer readable program, wherein the computer readable program when performed on a computer causes the computer to implement a method comprising:
receiving user profile information associated with a user as input by the user via a user interface of a client, wherein the user profile information includes user identification information, family information, health insurance information, medical information;
retrieving healthcare information from at least one external source and provide the retrieved healthcare information to the user at the user interface;
retrieve social service program information from a server interface, providing the retrieved social service program information to the user, and apply to at least one social service program of the server interface using the user profile information, when desired by the user;
retrieving interactive information to be presented to the user at the user interface, wherein the interactive information includes real-time information corresponding to online community information;
presenting the interactive information to the user via the user interface of the client;
retrieving at least one form for application to the at least one social service program when desired by the user;
automatically obtain user profile information associated with the user to complete the retrieved form for application to the at least one social service program;
submitting the completed form to the at least one host site; and
informing the user of a status of the application to the at least one social service program.

12. The transitory computer useable medium of claim 11, wherein the method further comprises:
providing interactive query usage by retrieving and organizing answers to a query performed by the user at the user interface.

13. The transitory computer useable medium of claim 12, wherein providing interactive query usage comprises:
generating a personalized query or a non-personalized query as selected by the user via the user interface; and
retrieving healthcare information specific to the user based on the user profile information when a personalized query is performed.

14. The transitory computer useable medium of claim 11, wherein the user profile information further comprises healthcare service information retrieved from third party sources and the healthcare information comprises healthcare educational information including chronic disease information and medical facility information.

* * * * *